(12) United States Patent
Malone et al.

(10) Patent No.: US 12,133,976 B2
(45) Date of Patent: Nov. 5, 2024

(54) PERCUTANEOUS CIRCULATORY SUPPORT DEVICE FACILITATING REDUCED HEMOLYSIS CLASS

(71) Applicant: Boston Scientific Scimed, Inc., Maple Grove, MN (US)

(72) Inventors: Anthony Malone, Galway (IE); Olena Pernatiy, Galway (IE); Javier Palomar-Moreno, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 91 days.

(21) Appl. No.: 17/992,149

(22) Filed: Nov. 22, 2022

(65) Prior Publication Data
US 2023/0158286 A1    May 25, 2023

Related U.S. Application Data

(60) Provisional application No. 63/282,207, filed on Nov. 23, 2021.

(51) Int. Cl.
*A61M 60/226* (2021.01)
*A61M 60/419* (2021.01)
(Continued)

(52) U.S. Cl.
CPC ........ *A61M 60/226* (2021.01); *A61M 60/419* (2021.01); *A61M 60/82* (2021.01); *F04D 13/024* (2013.01)

(58) Field of Classification Search
CPC ...... F04D 13/024; F04D 13/086; F04D 13/29; F04D 13/0467; F04D 13/048; A61M 60/82; A61M 60/419
See application file for complete search history.

(56) References Cited

U.S. PATENT DOCUMENTS 5,021,048 A    6/1991    Buckholtz
5,145,333 A    9/1992    Smith
(Continued)

FOREIGN PATENT DOCUMENTS

DE    3338002 A1    5/1985
EP    0847767 B1    2/2005
(Continued)

OTHER PUBLICATIONS

US 9,067,007 B2, 06/2015, Tanner et al. (withdrawn)
(Continued)

*Primary Examiner* — Kenneth J Hansen
(74) *Attorney, Agent, or Firm* — Seager, Tufte & Wickhem LLP (57) ABSTRACT

A percutaneous circulatory support device includes a housing having a proximal end portion and a motor carried by the housing. A driving magnet is operatively coupled to the motor, and a driven magnet is operatively coupled to the driving magnet. The driven magnet includes a frustoconical shape. An impeller is disposed within the housing, and the impeller is operatively coupled to the driven magnet. The motor rotates the impeller, via the driving magnet and the driven magnet, relative to the impeller housing to cause blood to flow through the percutaneous circulatory support device and blood is inhibited from pooling in the proximal end portion of the impeller housing.

20 Claims, 4 Drawing Sheets

(51) Int. Cl.
*A61M 60/82* (2021.01)
*F04D 13/02* (2006.01)

(56) References Cited

U.S. PATENT DOCUMENTS

| | | |
|---|---|---|
| 5,211,546 A | 5/1993 | Isaacson et al. |
| 5,527,159 A | 6/1996 | Bozeman, Jr. et al. |
| 5,611,679 A | 3/1997 | Ghosh et al. |
| 5,692,882 A | 12/1997 | Bozeman, Jr. et al. |
| 5,928,131 A | 7/1999 | Prem |
| 5,947,703 A | 9/1999 | Nojiri et al. |
| 5,947,892 A | 9/1999 | Benkowski et al. |
| 5,964,694 A | 10/1999 | Siess et al. |
| 6,056,520 A | 5/2000 | Nguyen et al. |
| 6,135,729 A | 10/2000 | Aber |
| 6,139,487 A | 10/2000 | Siess |
| 6,176,822 B1 | 1/2001 | Nix et al. |
| 6,176,848 B1 | 1/2001 | Rau et al. |
| 6,201,329 B1 | 3/2001 | Chen |
| 6,227,820 B1 | 5/2001 | Jarvik |
| 6,264,635 B1 | 7/2001 | Wampler et al. |
| 6,447,266 B2 | 9/2002 | Antaki et al. |
| 7,841,976 B2 | 11/2010 | McBride et al. |
| 7,927,068 B2 | 4/2011 | McBride et al. |
| 7,972,122 B2 | 7/2011 | Larose et al. |
| 8,007,254 B2 | 8/2011 | Larose et al. |
| 8,043,074 B2 | 10/2011 | Tada |
| 8,376,707 B2 | 2/2013 | McBride et al. |
| 8,512,012 B2 | 8/2013 | Akdis et al. |
| 8,591,393 B2 | 11/2013 | Walters et al. |
| 8,597,170 B2 | 12/2013 | Walters et al. |
| 8,684,904 B2 | 4/2014 | Campbell et al. |
| 8,721,517 B2 | 5/2014 | Zeng et al. |
| 8,770,945 B2 | 7/2014 | Ozaki et al. |
| 8,827,661 B2 | 9/2014 | Mori |
| 8,992,163 B2 | 3/2015 | McBride et al. |
| 9,067,005 B2 | 6/2015 | Ozaki et al. |
| 9,072,825 B2 | 7/2015 | Pfeffer et al. |
| 9,091,271 B2 | 7/2015 | Bourque |
| 9,138,518 B2 | 9/2015 | Yuen et al. |
| 9,162,017 B2 | 10/2015 | Evans et al. |
| 9,199,020 B2 | 12/2015 | Siess |
| 9,308,302 B2 | 4/2016 | Zeng |
| 9,308,304 B2 | 4/2016 | Peters et al. |
| 9,314,557 B2 | 4/2016 | Ricci et al. |
| 9,327,067 B2 | 5/2016 | Zeng et al. |
| 9,364,592 B2 | 6/2016 | McBride et al. |
| 9,364,593 B2 | 6/2016 | McBride et al. |
| 9,364,594 B2 | 6/2016 | Nsser et al. |
| 9,381,288 B2 | 7/2016 | Schenck et al. |
| 9,398,743 B1 | 7/2016 | Fox et al. |
| 9,421,311 B2 | 8/2016 | Tanner et al. |
| 9,446,179 B2 | 9/2016 | Keenan et al. |
| 9,616,157 B2 | 4/2017 | Akdis |
| 9,717,833 B2 | 8/2017 | McBride et al. |
| 9,737,652 B2 | 8/2017 | LaRose et al. |
| 9,770,543 B2 | 9/2017 | Tanner et al. |
| 9,872,947 B2 | 1/2018 | Keenan et al. |
| 9,895,476 B2 | 2/2018 | Larose et al. |
| 9,907,890 B2 | 3/2018 | Muller |
| 9,956,332 B2 | 5/2018 | Larose et al. |
| 9,962,475 B2 | 5/2018 | Yuen et al. |
| 9,964,115 B2 | 5/2018 | Scheckel |
| 10,029,037 B2 | 7/2018 | Muller et al. |
| 10,039,872 B2 | 8/2018 | Zeng et al. |
| 10,071,192 B2 | 9/2018 | Zeng |
| 10,086,121 B2 | 10/2018 | Fitzgerald et al. |
| 10,105,475 B2 | 10/2018 | Muller |
| 10,117,980 B2 | 11/2018 | Keenan et al. |
| 10,149,932 B2 | 12/2018 | McBride et al. |
| 10,215,187 B2 | 2/2019 | McBride et al. |
| 10,232,099 B2 | 3/2019 | Peters et al. |
| 10,251,985 B2 | 4/2019 | Larose et al. |
| 10,251,986 B2 | 4/2019 | Larose et al. |
| 10,478,539 B2 | 11/2019 | Pfeffer et al. |
| 10,478,540 B2 | 11/2019 | Scheckel et al. |
| 10,525,178 B2 | 1/2020 | Zeng |
| 10,576,192 B2 | 3/2020 | Muller et al. |
| 10,576,193 B2 | 3/2020 | Tanner et al. |
| 10,704,553 B2 | 7/2020 | Janeczek et al. |
| 10,709,829 B2 | 7/2020 | Muller |
| 10,709,830 B2 | 7/2020 | Tanner et al. |
| 10,765,789 B2 | 9/2020 | Zeng et al. |
| 10,780,208 B2 | 9/2020 | Siess et al. |
| 10,786,610 B2 | 9/2020 | Zeng |
| 10,799,624 B2 | 10/2020 | Pfeffer et al. |
| 10,842,921 B2 | 11/2020 | Siess et al. |
| 10,864,308 B2 | 12/2020 | Muller et al. |
| 10,864,309 B2 | 12/2020 | McBride et al. |
| 10,874,783 B2 | 12/2020 | Pfeffer et al. |
| 10,894,115 B2 | 1/2021 | Pfeffer et al. |
| 10,918,774 B2 | 2/2021 | Stanfield et al. |
| 10,960,116 B2 | 3/2021 | Yuen et al. |
| 10,973,967 B2 | 4/2021 | Nyikos et al. |
| 10,980,927 B2 | 4/2021 | Pfeffer et al. |
| 11,058,865 B2 | 7/2021 | Fitzgerald et al. |
| 11,097,092 B2 | 8/2021 | Siess et al. |
| 11,107,626 B2 | 8/2021 | Siess et al. |
| 11,123,539 B2 | 9/2021 | Pfeffer et al. |
| 11,129,978 B2 | 9/2021 | Pfeffer et al. |
| 11,167,124 B2 | 11/2021 | Pfeffer et al. |
| 11,219,755 B2 | 1/2022 | Siess et al. |
| 11,229,786 B2 | 1/2022 | Zeng et al. |
| 11,235,138 B2 | 2/2022 | Gross-Hardt et al. |
| 11,253,693 B2 | 2/2022 | Pfeffer et al. |
| 11,260,213 B2 | 3/2022 | Zeng et al. |
| 11,273,301 B2 | 3/2022 | Pfeffer et al. |
| 11,311,712 B2 | 4/2022 | Zeng et al. |
| 11,338,124 B2 | 5/2022 | Pfeffer et al. |
| 11,357,967 B2 | 6/2022 | Zeng et al. |
| 11,400,276 B2 | 8/2022 | Chopra et al. |
| 11,471,664 B2 | 10/2022 | Xu et al. |
| 11,497,896 B2 | 11/2022 | Tanner et al. |
| 11,517,736 B2 | 12/2022 | Earles et al. |
| 11,569,015 B2 | 1/2023 | Mourran et al. |
| 11,583,659 B2 | 2/2023 | Pfeffer et al. |
| 11,628,294 B2 | 4/2023 | Chopra et al. |
| 11,648,388 B2 * | 5/2023 | Siess .............. A61M 60/865 623/3.13 |
| 11,672,968 B2 | 6/2023 | Antaki |
| 11,708,833 B2 | 7/2023 | McBride et al. |
| 11,754,075 B2 | 9/2023 | Schuelke et al. |
| 11,786,700 B2 | 10/2023 | Pfeffer et al. |
| 11,813,443 B2 | 11/2023 | Hanson et al. |
| 2003/0233021 A1 | 12/2003 | Nose et al. |
| 2006/0222533 A1 | 10/2006 | Reeves et al. |
| 2008/0114339 A1 | 5/2008 | McBride et al. |
| 2009/0060743 A1 | 3/2009 | McBride et al. |
| 2009/0093764 A1 | 4/2009 | Pfeffer et al. |
| 2009/0171137 A1 | 7/2009 | Farnan et al. |
| 2011/0237863 A1 | 9/2011 | Ricci et al. |
| 2011/0238172 A1 | 9/2011 | Akidis |
| 2013/0338559 A1 | 12/2013 | Franano et al. |
| 2014/0005467 A1 | 1/2014 | Farnan et al. |
| 2014/0010686 A1 | 1/2014 | Tanner et al. |
| 2014/0336446 A1 | 11/2014 | Rodefield |
| 2016/0271308 A1 | 9/2016 | LaRose et al. |
| 2017/0043074 A1 | 2/2017 | Siess |
| 2017/0296725 A1 | 10/2017 | Peters et al. |
| 2018/0303990 A1 | 10/2018 | Siess et al. |
| 2018/0311423 A1 | 11/2018 | Zeng et al. |
| 2019/0275224 A1 | 9/2019 | Hanson et al. |
| 2020/0306434 A1 | 10/2020 | Vancamp et al. |
| 2021/0015982 A1 | 1/2021 | Kerkhoffs et al. |
| 2021/0023282 A1 | 1/2021 | Siess et al. |
| 2021/0038785 A1 | 2/2021 | Siess et al. |
| 2021/0069393 A1 | 3/2021 | Schauer et al. |
| 2021/0106810 A1 | 4/2021 | Pfeffer et al. |
| 2022/0134082 A1 | 5/2022 | Pfeffer et al. |
| 2022/0384070 A1 | 12/2022 | Mourran |

(56) References Cited

U.S. PATENT DOCUMENTS

2023/0040593 A1    2/2023  Liu et al.
2024/0075275 A1*   3/2024  Earles ................. A61M 60/221

FOREIGN PATENT DOCUMENTS

| EP | 2301598 | B1 | 7/2017 |
| EP | 3352808 | B1 | 9/2023 |
| WO | 9500185 | A1 | 1/1995 |
| WO | 0117581 | A2 | 3/2001 |
| WO | 2018197306 | A1 | 11/2018 |
| WO | 2019135767 | A1 | 7/2019 |
| WO | 2021113389 | A1 | 6/2021 |

OTHER PUBLICATIONS

International Search Report and Written Opinion for International Application No. PCT/US2022/050053 dated Mar. 6, 2023. (14 pages).
International Search Report and Written Opinion for International Application No. PCT/US2022/050694 dated Apr. 5, 2023. (14 pages).

* cited by examiner

PERCUTANEOUS CIRCULATORY SUPPORT DEVICE FACILITATING REDUCED HEMOLYSIS CLASS

CROSS REFERENCE TO RELATED APPLICATION

This application claims priority to Provisional Application No. 63/282,207, filed Nov. 23, 2021, which is herein incorporated by reference in its entirety.

TECHNICAL FIELD

The present disclosure relates to percutaneous circulatory support systems. More specifically, the disclosure relates to percutaneous circulatory support devices that facilitate reduced hemolysis and/or related complications.

BACKGROUND

Percutaneous circulatory support devices such as devices can provide transient support for up to approximately several weeks in patients with compromised heart function or cardiac output. Operation of such devices, however, may cause some amount of hemolysis (that is, the rupture or destroying of blood cells) or other complications. Hemolysis can in turn cause thrombi formation or other complications. Accordingly, there is a need for improved devices that facilitate reduced hemolysis and/or related complications.

SUMMARY

In an Example 1, a percutaneous circulatory support device comprises a housing comprising a proximal end portion; a motor carried by the housing; a driving magnet operatively coupled to the motor; a driven magnet operatively coupled to the driving magnet; the driven magnet comprising a frustoconical shape; and an impeller disposed within the housing, the impeller being operatively coupled to the driven magnet.

In an Example 2, the percutaneous circulatory support device of Example 1, further comprising an outlet, and wherein the driven magnet is disposed apart from the outlet to define an inverse frustoconical chamber in the housing.

In an Example 3, the percutaneous circulatory support device of either of Examples 1 or 2, further comprising an impeller shaft being fixed relative to the impeller and the driven magnet.

In an Example 4, the percutaneous circulatory support device of any of Examples 1 to 3, further comprising a bearing disposed between the driving magnet and the driven magnet.

In an Example 5, the percutaneous circulatory support device of any of Examples 1 to 4, wherein the driven magnet tapers radially inwardly proceeding in a proximal direction.

In an Example 6, the percutaneous circulatory support device of any of Examples 1 to 4, wherein the driven magnet tapers radially inwardly proceeding in a distal direction.

In an Example 7, the percutaneous circulatory support device of any of Examples 1 to 6, wherein the housing comprises a plurality of outlet apertures each extending to a proximal end of the driven magnet.

In an Example 8, the percutaneous circulatory support device of any of Examples 1 to 7, wherein a proximal portion of the impeller comprises a flattened shape.

In an Example 9, a percutaneous circulatory support device comprises a housing comprising a proximal end portion, an inlet, and an outlet; a motor carried by the housing; a driving magnet operatively coupled to the motor; a driven magnet operatively coupled to the driving magnet; the driven magnet comprising a frustoconical shape and being disposed apart from the outlet to define an inverse frustoconical chamber in the proximal end portion of the housing; and an impeller disposed within the housing, the impeller being operatively coupled to the driven magnet.

In an Example 10, the percutaneous circulatory support device of Example 9, further comprising an impeller shaft being fixed relative to the impeller and the driven magnet.

In an Example 11, the percutaneous circulatory support device of either of Examples 9 or 10, wherein the driven magnet tapers radially inwardly proceeding in a proximal direction.

In an Example 12, the percutaneous circulatory support device of either of Examples 9 or 10, wherein the driven magnet tapers radially inwardly proceeding in a distal direction.

In an Example 13, the percutaneous circulatory support device of any of Examples 9 to 12, wherein the outlet comprises a plurality of outlet apertures each extending to a proximal end of the driven magnet.

In an Example 14, the percutaneous circulatory support device of any of Examples 9 to 13, wherein a proximal portion of the impeller comprises a flattened shape.

In an Example 15, the percutaneous circulatory support device of any of Examples 9 to 14, wherein the housing comprises a motor housing carrying the motor and an impeller housing carrying the impeller.

In an Example 16, a percutaneous circulatory support device comprises an impeller housing comprising a proximal end portion; a motor housing coupled to the impeller housing; a motor carried by the motor housing; a driving magnet operatively coupled to the motor; a driven magnet operatively coupled to the driving magnet; the driven magnet comprising a frustoconical shape; and an impeller disposed within the impeller housing, the impeller being operatively coupled to the driven magnet; wherein the motor rotates the impeller, via the driving magnet and the driven magnet, relative to the impeller housing to cause blood to flow through the percutaneous circulatory support device and blood is inhibited from pooling in the proximal end portion of the impeller housing.

In an Example 17, the percutaneous circulatory support device of Example 16, further comprising an outlet, and wherein the driven magnet is disposed apart from the outlet to define an inverse frustoconical chamber in the impeller housing.

In an Example 18, the percutaneous circulatory support device of Example 16, further comprising an impeller shaft being fixed relative to the impeller and the driven magnet.

In an Example 19, the percutaneous circulatory support device of Example 16, wherein the driving magnet is disposed within the motor housing and the driven magnet is disposed within the impeller housing.

In an Example 20, the percutaneous circulatory support device of Example 16, further comprising a bearing disposed between the driving magnet and the driven magnet.

In an Example 21, the percutaneous circulatory support device of Example 16, wherein the driven magnet tapers radially inwardly proceeding in a proximal direction.

In an Example 22, the percutaneous circulatory support device of Example 16, wherein the driven magnet tapers radially inwardly proceeding in a distal direction.

In an Example 23, the percutaneous circulatory support device of Example 16, wherein the impeller housing comprises a plurality of outlet apertures each extending to a proximal end of the driven magnet.

In an Example 24, the percutaneous circulatory support device of Example 16, wherein a proximal portion of the impeller comprises a flattened shape.

In an Example 25, a percutaneous circulatory support device comprises an impeller housing comprising a proximal end portion, an inlet, and an outlet; a motor housing coupled to the impeller housing; a motor carried by the motor housing; a driving magnet operatively coupled to the motor; a driven magnet operatively coupled to the driving magnet; the driven magnet comprising a frustoconical shape and being disposed apart from the outlet to define an inverse frustoconical chamber in the proximal end portion of the impeller housing; and an impeller disposed within the impeller housing, the impeller being operatively coupled to the driven magnet; wherein the motor rotates the impeller, via the driving magnet and the driven magnet, relative to the impeller housing to cause blood to flow through the percutaneous circulatory support device and blood is inhibited from pooling in the proximal end portion of the impeller housing.

In an Example 26, the percutaneous circulatory support device of Example 25, further comprising an impeller shaft being fixed relative to the impeller and the driven magnet.

In an Example 27, the percutaneous circulatory support device of Example 25, wherein the driven magnet tapers radially inwardly proceeding in a proximal direction.

In an Example 28, the percutaneous circulatory support device of Example 25, wherein the driven magnet tapers radially inwardly proceeding in a distal direction.

In an Example 29, the percutaneous circulatory support device of Example 25, wherein the outlet comprises a plurality of outlet apertures each extending to a proximal end of the driven magnet.

In an Example 30, the percutaneous circulatory support device of Example 25, wherein a proximal portion of the impeller comprises a flattened shape.

In an Example 31, a method for using a percutaneous circulatory support device comprises positioning the percutaneous circulatory support device at a target location within a patient; rotating an impeller of the percutaneous circulatory support device, via a motor, a driving magnet, and a driven magnet comprising a frustoconical shape, to cause blood to flow through the percutaneous circulatory support device, wherein blood is inhibited from pooling in a proximal end portion of an impeller housing of the percutaneous circulatory support device.

In an Example 32, the method of Example 31, wherein rotating the impeller and rotating the driven magnet comprise rotating the impeller and the driven magnet together relative to the impeller housing.

In an Example 33, the method of Example 31, wherein the driven magnet tapers radially inwardly proceeding in a proximal direction.

In an Example 34, the method of Example 31, wherein the driven magnet tapers radially inwardly proceeding in a proximal direction.

In an Example 35, the method of Example 31, wherein the percutaneous circulatory support device further comprises an outlet, and the outlet comprises a plurality of outlet apertures each extending to a proximal end of the driven magnet.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
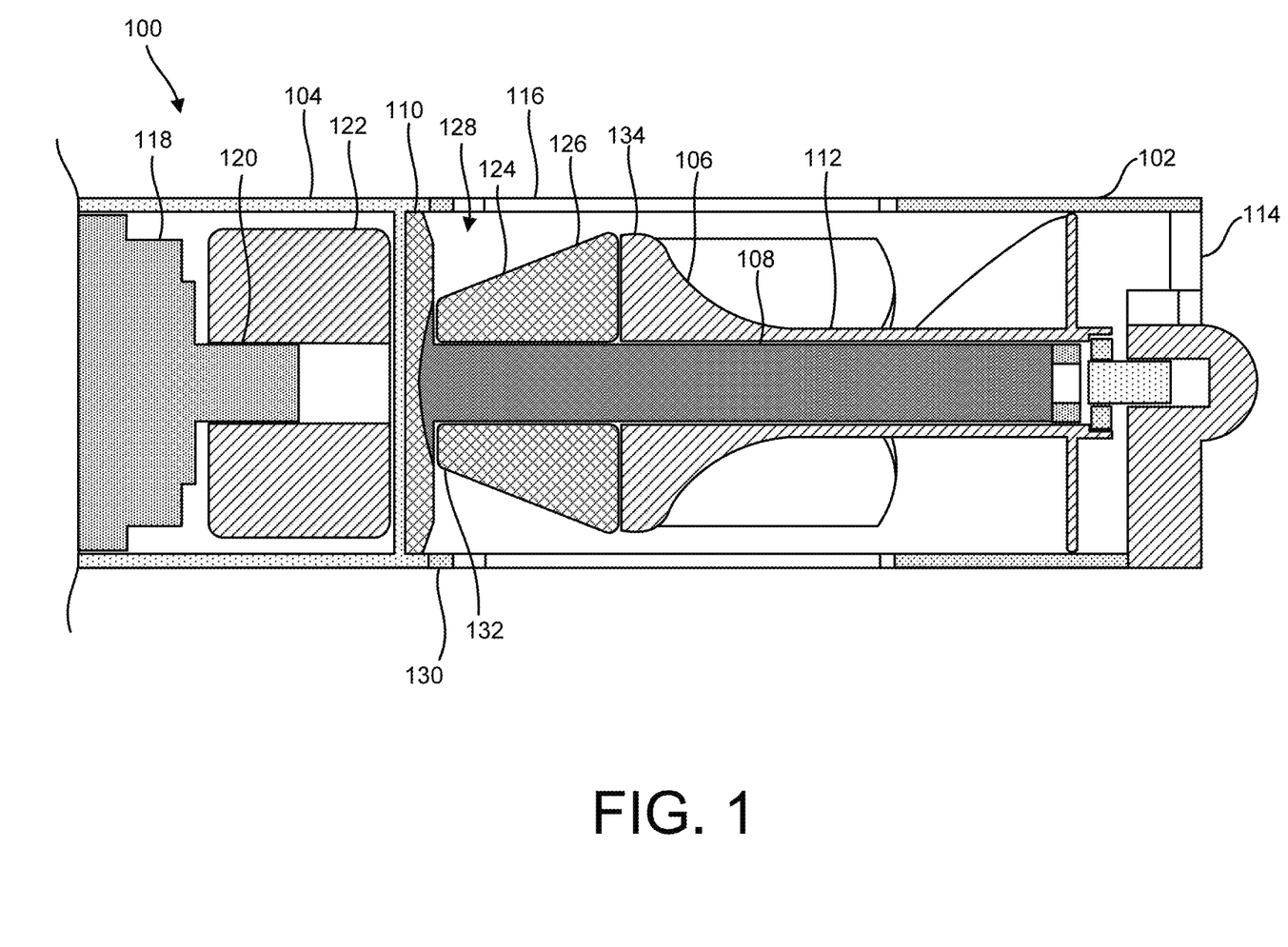
FIG. 1 is a side sectional view of an illustrative mechanical circulatory support device (also referred to herein, interchangeably, as a "blood pump"), in accordance with embodiments of the subject matter disclosed herein.

FIG. 1 depicts a partial side sectional view of an illustrative mechanical circulatory support device 100 (also referred to herein, interchangeably, as a "blood pump") in accordance with embodiments of the subject matter disclosed herein. The device 100 may form part of a percutaneous circulatory support system, together with a guidewire and an introducer sheath (not shown). More specifically, the guidewire and the introducer sheath may facilitate percutaneously delivering the device 100 to a target location within a patient, such as within the patient's heart. Alternatively, the device 100 may be delivered to a different target location within a patient.

Figure 2:
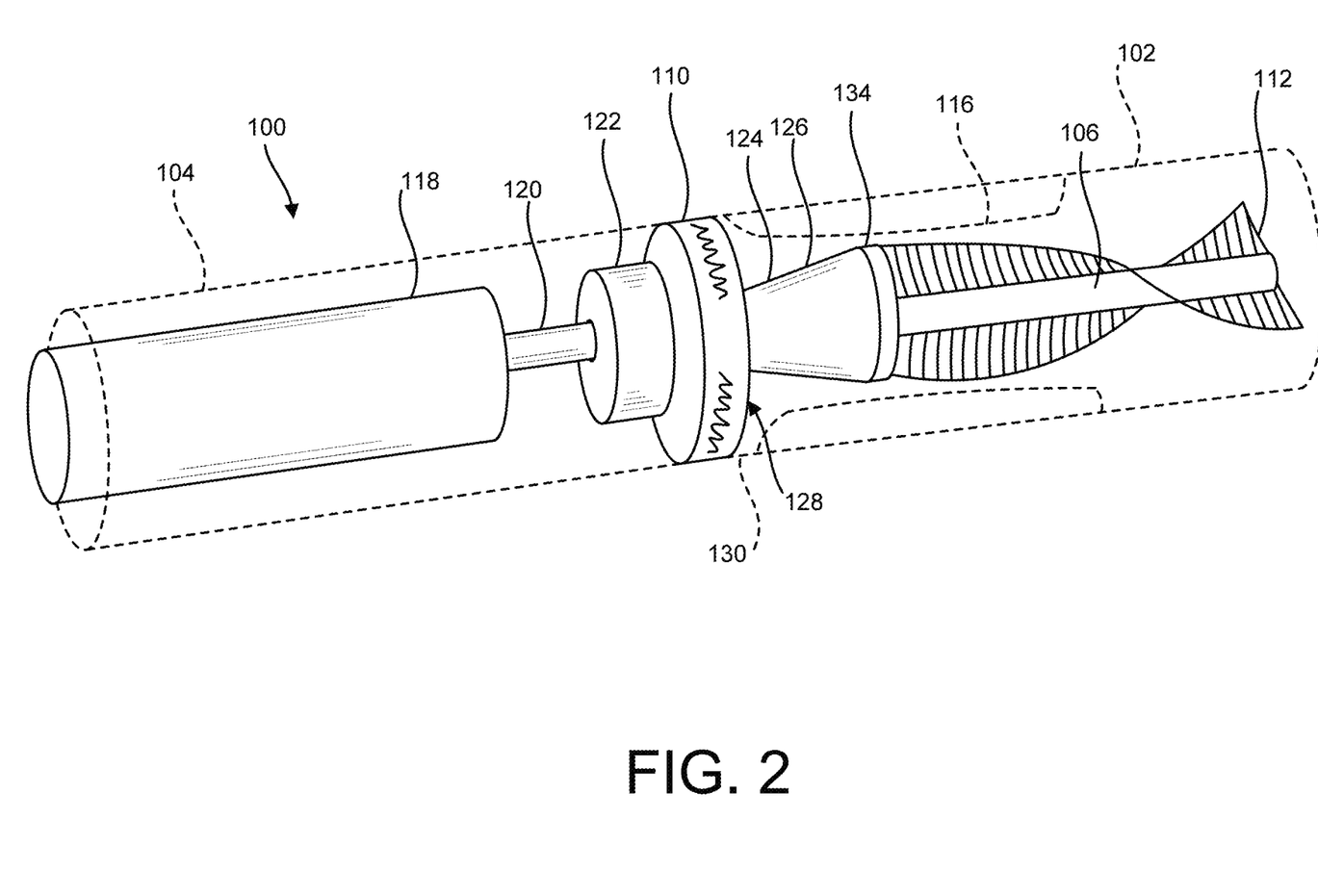
FIG. 2 is a perspective view of the mechanical circulatory support device of FIG. 1, with housing components of the device shown in phantom lines, in accordance with embodiments of the subject matter disclosed herein.

With continued reference to FIG. 1 and additional reference to FIG. 2, the device 100 generally includes an impeller housing 102 and a motor housing 104. In some embodiments, the impeller housing 102 and the motor housing 104 may be integrally or monolithically constructed. In other embodiments, the impeller housing 102 and the motor housing 104 may be separate components configured to be removably or permanently coupled.

The impeller housing 102 carries an impeller assembly 106 therein. The impeller assembly 106 includes an impeller shaft 108 (FIG. 1) that is rotatably supported by at least one bearing, such as a bearing 110. The impeller assembly 106 also includes an impeller 112 that rotates relative to the impeller housing 102 to drive blood through the device 100. More specifically, the impeller 112 causes blood to flow from a blood inlet 114 (FIG. 1) formed on the impeller housing 102, through the impeller housing 102, and out of a blood outlet 116 formed on the impeller housing 102. In some embodiments and as illustrated, the impeller shaft 108 and the impeller 112 may be separate components, and in other embodiments the impeller shaft 108 and the impeller 112 may be integrated. In some embodiment and as illustrated, the inlet 114 and/or the outlet 116 may each include multiple apertures. In other embodiments, the inlet 114 and/or the outlet 116 may each include a single aperture. In some embodiments and as illustrated, the inlet 114 may be formed on an end portion of the impeller housing 102 and the outlet 116 may be formed on a side portion of the impeller housing 102. In other embodiments, the inlet 114 and/or the outlet 116 may be formed on other portions of the impeller housing 102. In some embodiments, the impeller housing 102 may couple to a distally extending cannula (not shown), and the cannula may receive and deliver blood to the inlet 114.

With continued reference to FIGS. 1 and 2, the motor housing 104 carries a motor 118, and the motor 118 is configured to rotatably drive the impeller 112 relative to the impeller housing 102. In the illustrated embodiment, the motor 118 rotates a drive shaft 120, which is coupled to a driving magnet 122. Rotation of the driving magnet 122 causes rotation of a driven magnet 124, which is connected to and rotates together with the impeller assembly 106. More specifically, in embodiments incorporating the impeller shaft 108, the impeller shaft 108 and the impeller 112 are configured to rotate with the driven magnet 124. In other embodiments, the motor 118 may couple to the impeller assembly 106 via other components.

In some embodiments, a controller (not shown) may be operably coupled to the motor 118 and configured to control the motor 118. In some embodiments, the controller may be disposed within the motor housing 104. In other embodiments, the controller may be disposed outside of the motor housing 104 (for example, in a catheter handle, an independent housing, etc.). In some embodiments, the controller may include multiple components, one or more of which may be disposed within the motor housing 104. According to embodiments, the controller may be, may include, or may be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more Central Processing Units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like. In other embodiments, the motor 118 may be controlled in other manners.

With further reference to FIGS. 1 and 2, the device 100 facilitates reduced device-induced hemolysis compared to conventional devices. More specifically, the driven magnet 124 includes an outer surface 126 that has a frustoconical shape. The frustoconical outer surface 126 is disposed apart from the outlet 116 and thereby defines an inverse frustoconical chamber 128 in a proximal end portion 130 of the impeller housing 102. The chamber 128 is relatively large compared to the small spaces between the driven magnet and the impeller housing in a conventional device. As a result, rotation of the driven magnet 124 inhibits blood from pooling in the inverse frustoconical chamber 128, which reduces hemolysis and/or thrombosis. In some embodiments, the frustoconical outer surface 126 of the driven magnet 124 tapers radially inwardly proceeding in a proximal direction. In other embodiments and as shown elsewhere, the frustoconical outer surface 126 of the driven magnet 124 tapers radially inwardly proceeding in a distal direction.

The device 100 may also include one or more additional features that facilitate reduced device-induced hemolysis compared to conventional devices. For example, the apertures of the outlet 116 may be relatively long compared to those of conventional devices. More specifically, the apertures of the outlet 116 may each extend to a proximal end 132 (FIG. 1) of the driven magnet 124. Such apertures further inhibit blood from pooling in the proximal end portion 130 of the impeller housing 102, which reduces hemolysis and/or thrombosis. As another example, a proximal end portion 134 of the impeller 112 may have a flattened shape, in contrast to lips or peaks of the impellers of conventional devices. Such a shape inhibits blood from forming and pooling in vortices adjacent to the impeller 112.

Figure 3:
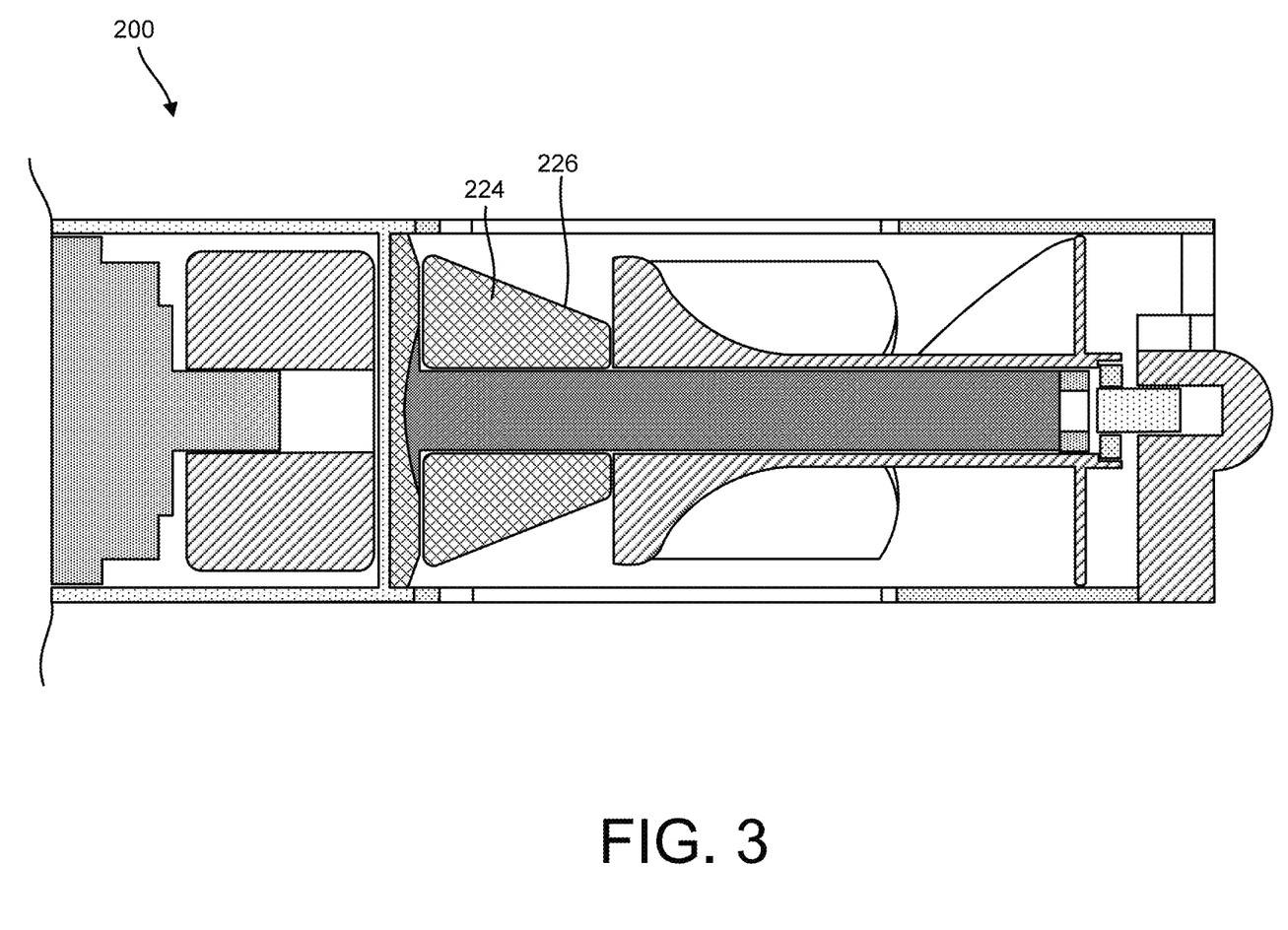
FIG. 3 is a side sectional view of another illustrative mechanical circulatory support device, in accordance with embodiments of the subject matter disclosed herein.
Figure 4:
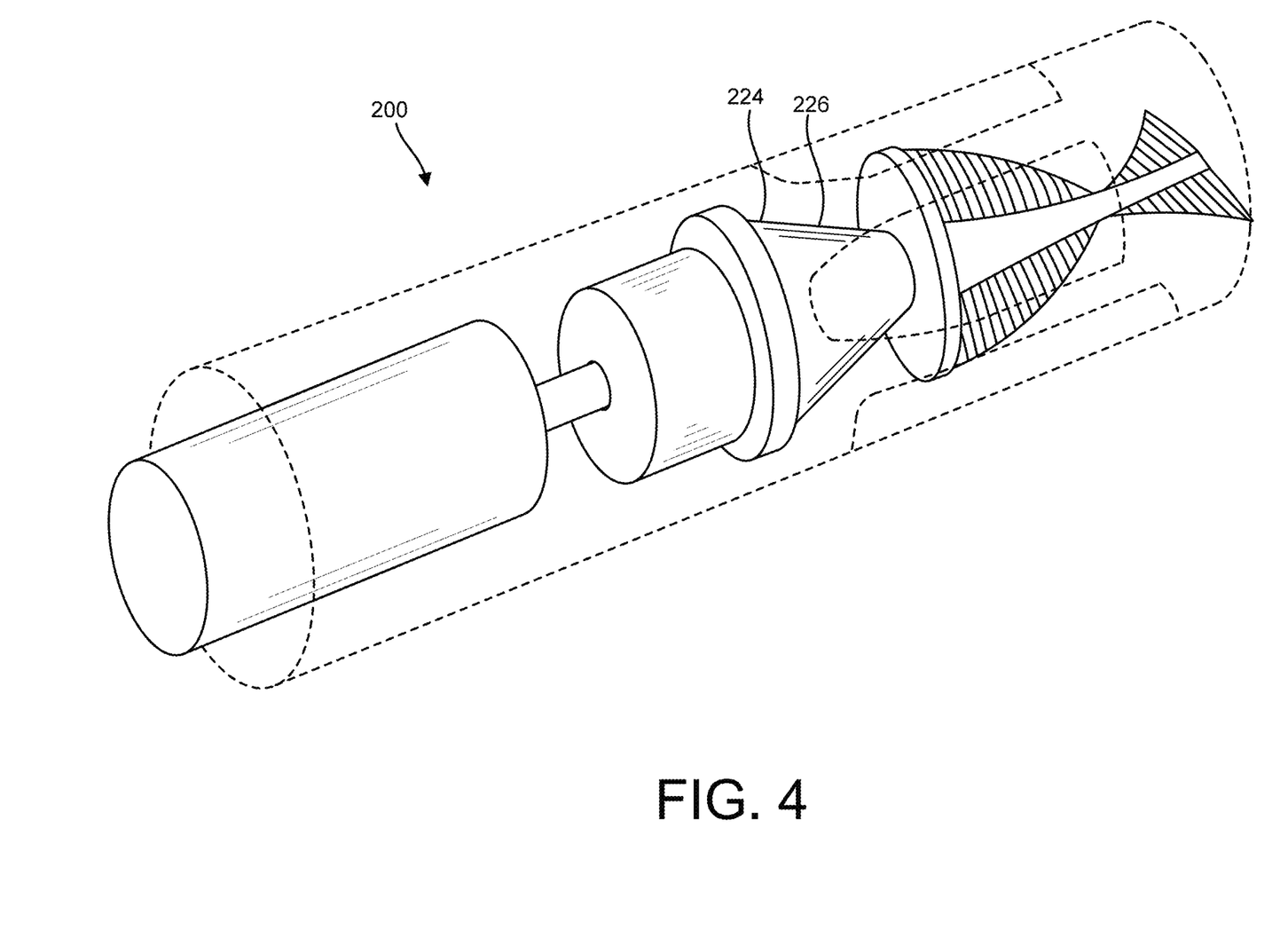
FIG. 4 is a perspective view of the mechanical circulatory support device of FIG. 3, with housing components of the device shown in phantom lines, in accordance with embodiments of the subject matter disclosed herein.

FIGS. 3 and 4 depict another illustrative mechanical circulatory support device 200 in accordance with embodiments of the subject matter disclosed herein. The device 200 includes the same features and components as the device 100, except that the frustoconical outer surface 226 of the driven magnet 224 tapers radially inwardly proceeding in a distal direction.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A percutaneous circulatory support device, comprising:
an impeller housing comprising a proximal end portion;
a motor housing coupled to the impeller housing;
a motor carried by the motor housing;
a driving magnet operatively coupled to the motor;
a driven magnet operatively coupled to the driving magnet; the driven magnet comprising a frustoconical shape; wherein a portion of a radially outward facing surface of the driven magnet is tapered; and
an impeller disposed within the impeller housing, the impeller being operatively coupled to the driven magnet;
wherein the motor rotates the impeller, via the driving magnet and the driven magnet, relative to the impeller housing to cause blood to flow through the percutaneous circulatory support device and blood is inhibited from pooling in the proximal end portion of the impeller housing.

2. The percutaneous circulatory support device of claim 1, further comprising an outlet, and wherein the driven magnet is disposed apart from the outlet to define an inverse frustoconical chamber in the impeller housing.

3. The percutaneous circulatory support device of claim 1, further comprising an impeller shaft being fixed relative to the impeller and the driven magnet.

4. The percutaneous circulatory support device of claim 1, wherein the driving magnet is disposed within the motor housing and the driven magnet is disposed within the impeller housing.

5. The percutaneous circulatory support device of claim 1, further comprising a bearing disposed between the driving magnet and the driven magnet.

6. The percutaneous circulatory support device of claim 1, wherein the driven magnet tapers radially inwardly proceeding in a proximal direction.

7. The percutaneous circulatory support device of claim 1, wherein the driven magnet tapers radially inwardly proceeding in a distal direction.

8. The percutaneous circulatory support device of claim 1, wherein the impeller housing comprises a plurality of outlet apertures each extending to a proximal end of the driven magnet.

9. The percutaneous circulatory support device of claim 1, wherein a proximal portion of the impeller comprises a flattened shape.

10. A percutaneous circulatory support device, comprising:
    an impeller housing comprising a proximal end portion, an inlet, and an outlet;
    a motor housing coupled to the impeller housing;
    a motor carried by the motor housing;
    a driving magnet operatively coupled to the motor;
    a driven magnet operatively coupled to the driving magnet; the driven magnet comprising a frustoconical shape; wherein a portion of a radially outward facing surface of the driven magnet is tapered; the driven magnet being disposed apart from the outlet to define an inverse frustoconical chamber in the proximal end portion of the impeller housing; and
    an impeller disposed within the impeller housing, the impeller being operatively coupled to the driven magnet;
    wherein the motor rotates the impeller, via the driving magnet and the driven magnet, relative to the impeller housing to cause blood to flow through the percutaneous circulatory support device and blood is inhibited from pooling in the proximal end portion of the impeller housing.

11. The percutaneous circulatory support device of claim 10, further comprising an impeller shaft being fixed relative to the impeller and the driven magnet.

12. The percutaneous circulatory support device of claim 10, wherein the driven magnet tapers radially inwardly proceeding in a proximal direction.

13. The percutaneous circulatory support device of claim 10, wherein the driven magnet tapers radially inwardly proceeding in a distal direction.

14. The percutaneous circulatory support device of claim 10, wherein the outlet comprises a plurality of outlet apertures each extending to a proximal end of the driven magnet.

15. The percutaneous circulatory support device of claim 10, wherein a proximal portion of the impeller comprises a flattened shape.

16. A method for using a percutaneous circulatory support device, comprising:
    positioning the percutaneous circulatory support device at a target location within a patient;
    rotating an impeller of the percutaneous circulatory support device, via a motor, a driving magnet, and a driven magnet comprising a frustoconical shape, wherein a portion of radially outward facing surface of the driven magnet is tapered, to cause blood to flow through the percutaneous circulatory support device, wherein blood is inhibited from pooling in a proximal end portion of an impeller housing of the percutaneous circulatory support device.

17. The method of claim 16, wherein rotating the impeller and rotating the driven magnet comprise rotating the impeller and the driven magnet together relative to the impeller housing.

18. The method of claim 16, wherein the driven magnet tapers radially inwardly proceeding in a proximal direction.

19. The method of claim 16, wherein the driven magnet tapers radially inwardly proceeding in a distal direction.

20. The method of claim 16, wherein the percutaneous circulatory support device further comprises an outlet, and the outlet comprises a plurality of outlet apertures each extending to a proximal end of the driven magnet.

* * * * *

UNITED STATES PATENT AND TRADEMARK OFFICE
CERTIFICATE OF CORRECTION

| | | |
|---|---|---|
| PATENT NO. | : 12,133,976 B2 | Page 1 of 1 |
| APPLICATION NO. | : 17/992149 | |
| DATED | : November 5, 2024 | |
| INVENTOR(S) | : Anthony Malone et al. | |

It is certified that error appears in the above-identified patent and that said Letters Patent is hereby corrected as shown below:

On the Title Page

Item (54) and in the Specification Column 1, Lines 1-3, The title should read:
PERCUTANEOUS CIRCULATORY SUPPORT DEVICE FACILITATING REDUCED HEMOLYSIS Signed and Sealed this
Tenth Day of December, 2024

Katherine Kelly Vidal
*Director of the United States Patent and Trademark Office*